United States Patent [19]

Wong et al.

[11] Patent Number: 4,663,292
[45] Date of Patent: May 5, 1987

[54] HIGH-VOLTAGE BIOLOGICAL MACROMOLECULE TRANSFER AND CELL FUSION SYSTEM

[76] Inventors: Daniel T. Wong, 18866 Allendale Ave., Saratoga, Calif. 95070; Tai-Kin Wong, 18641 Crabtree Ave., Cupertino, Calif. 95014

[21] Appl. No.: 684,599

[22] Filed: Dec. 21, 1984

[51] Int. Cl.$^4$ .............................................. C12M 1/00
[52] U.S. Cl. ................................ 435/287; 435/172.3; 935/52; 328/158
[58] Field of Search ........................... 435/287, 172.3; 328/158; 935/52

[56] References Cited

U.S. PATENT DOCUMENTS 3,659,226  4/1972  Angeleri ........................ 328/158 X
3,758,873  9/1973  Miller .............................. 328/158 X

OTHER PUBLICATIONS

W. Anderson, "Prospect for Human Gene Therapy," 226 *Science* 401 (Oct. 26, 1984).
G. Scangos and F. Ruddle, "Mechanisms and Applications of DNA-Mediated Gene Transfer in Mammalian Cells—a review," 14 *Gene* 1 (1981).
U. Zimmerman and J. Greyson, "Electric Field-Induced Cell Fusion," *Biotechniques* (Sep./Oct. 1983).
T. Wong and E. Neumann, "Electric Field Mediated Gene Transfer," 107 *Biochem. & Biophys. Res. Comm.*, 584–587 (Jul. 30, 1982).

*Primary Examiner*—Alan Cohan
*Attorney, Agent, or Firm*—Limbach, Limbach & Sutton

[57] ABSTRACT

A high-voltage biological macromolecule transfer and cell fusion system for transforming a low input voltage into a high-voltage discharge output. The system comprises voltages source means, a frequency source means, a burst control means, a cycle control means, a pulse generating means, a pulse control means, and a high-voltage discharge generating means. The voltages source means is adapted to transform the generally low input voltage into a system-enabling control signal, a direct-current base voltage, and a generally low-voltage direct-current system voltage. The frequency source means generates system-enabling control pulses. The burst control means is provided to control the burst time of the high-voltage discharge output. The cycle control means is adapted to control the number of cycles in the high-voltage discharge output. The pulse generating means generates the pulses that evolve into the high-voltage discharge output. The pulse control means is adapted to control the number of pulses within each cycle of the high-voltage discharge output. The burst control means, the cycle control means, the pulse generating means and the pulse control means produce a composite signal. The high-voltage discharge generating means is provided for transforming the low-voltage system voltage and the composite signal into the high-voltage discharge output.

7 Claims, 6 Drawing Figures

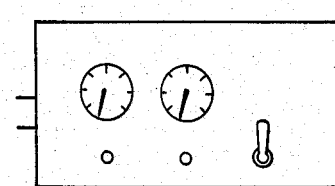
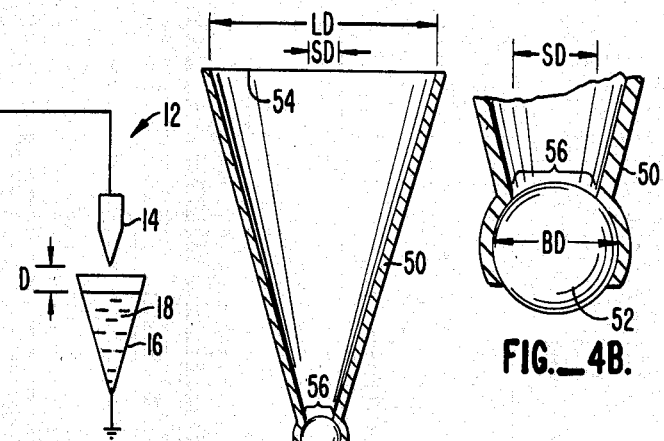
FIG._1.   FIG._4A.   FIG._4B.
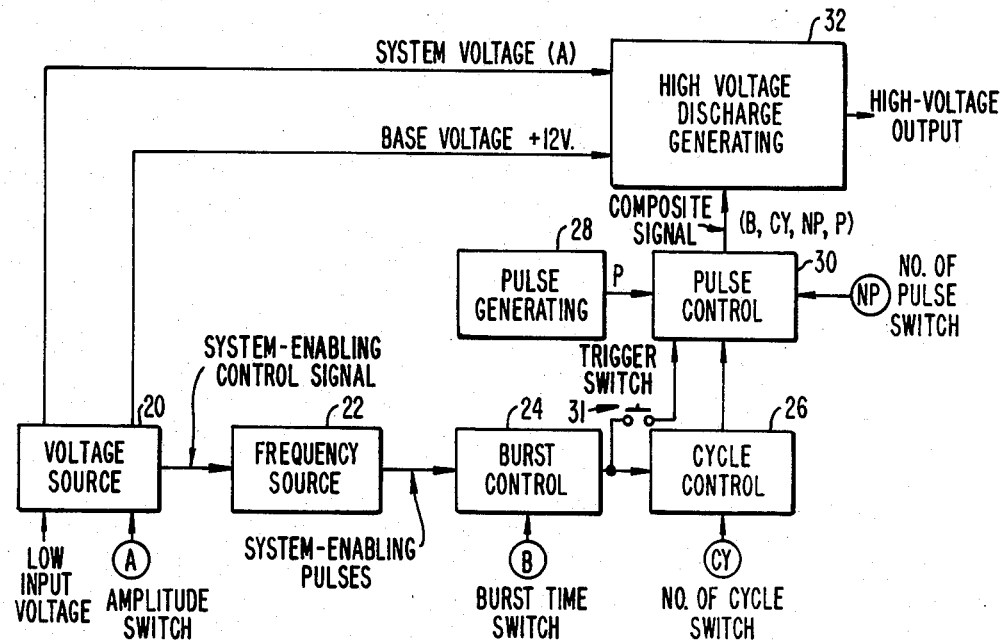
FIG._2.

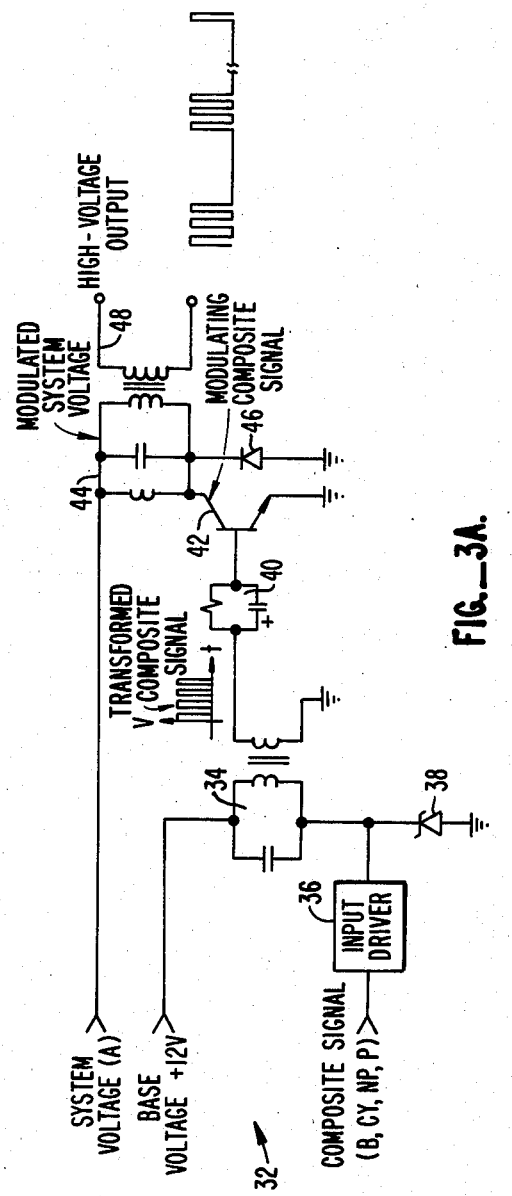
FIG._3A.
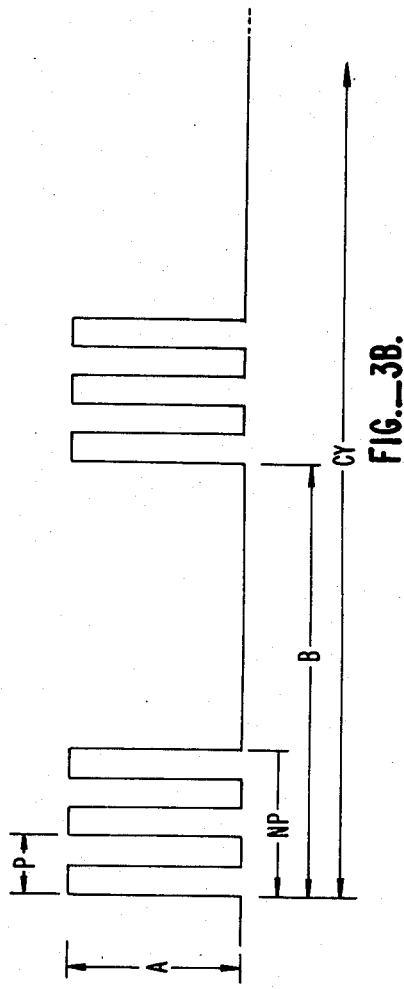
FIG._3B.

HIGH-VOLTAGE BIOLOGICAL MACROMOLECULE TRANSFER AND CELL FUSION SYSTEM

DESCRIPTION

1. Technical Field

This invention relates to systems for transferring biological molecules into cells and more particularly, to a high-voltage system capable of performing both biological macromolecule transfers and cell fusions.

2. Background Art

In the field of biotechnology, there has been recent advances in the techniques for transferring biological macromolecules such as genes into cells. Biological macromolecules are defined as those molecules which cannot be readily diffused through cell membranes; those macromolecules include DNA, RNA, protein, etc. Some examples of gene transfers are described in G. Scangos and F. Ruddle, "Mechanisms and applications of DNA-mediated gene transfer in mammalian cells - a review," 14 *Gene* 1 (1981); and W. Anderson, "Prospects for Human Gene Therapy," 226 *Science* 401 (Oct. 26, 1984).

One method of transferring genes into cells is the use of electric field pulses. This method is based on the observation that electric pulses above a certain threshold field strength would induce reversible electrical breakdown of cell membranes, resulting in the creation of pores in the membranes. The pores are of sufficient dimension as to permit the entry of genes into the cells. Such a method is described in T. Wong and E. Neumann, "Electric Field Mediated Gene Transfer," 107 *Biochemical and Biophysical Research Communications* 584 (July 30, 1982).

The ideal high-voltage biological macromolecule transfer system should be capable of permitting the ready adjustment of operating parameters. In addition, the system should be capable of providing a continuous output of discharging pulses. Moreover, the system should have non-contact discharging to eliminate the likelihood of contaminating the cell suspension. Further, the entire procedure should be simple and the time to complete the entire procedure should not be time consuming.

DISCLOSURE OF THE INVENTION

It is a major object of the present invention to provide a novel high-voltage biological macromolecule transfer and cell fusion system.

It is another object of the present invention to provide a novel biological macromolecule transfer and cell fusion system the operating parameters for which are readily adjustable.

It is a further object of the present invention to provide a novel biological macromolecule transfer and cell fusion system that is capable of providing a continuous output of discharging pulses.

It is another object of the present invention to provide a novel biological macromolecule transfer and cell fusion system that is capable of non-contact discharging, eliminating the likelihood of contaminating the suspension.

It is a still further object of the present invention to provide a novel biological macromolecule transfer and cell fusion system the operating procedure for which is simple and the time to complete the procedure is short.

It is another object of the present invention to provide a novel biological macromolecule transfer and cell fusion system that includes a novel cell suspension receptacle.

In order to accomplish the above and still further objects, the present invention provides a novel high-voltage biological macromolecule transfer and cell fusion system. The biological macromolecule transfer and cell fusion system, which is adapted to transform a low input voltage into a high-voltage discharge output, comprises voltages source means, a frequency source means, a burst control means, a cycle control means, a pulse generating means, a pulse control means, and a high-voltage discharge generating means.

More particularly, the voltages source means is adapted to transform a generally low input voltage into a system-enabling control signal, a direct-current base voltage, and a generally low-voltage direct-current system voltage. The frequency source means is adapted to transform the control signal into system-enabling control pulses. The burst control means is adapted to control the burst time of the high voltage discharge output. The cycle control means is adapted to control the number of cycles in the high-voltage discharge output. The pulse generating means generates pulses. The pulse control means controls the number of necessary pulses within each cycle of the high-voltage output discharge. The burst control means, the cycle control means, the pulse generating means and the pulse control means produce a composite signal. The high-voltage discharge generating means is adapted to transform the low-voltage system voltage and the composite signal into the high-voltage discharge output, whereby the high-voltage discharge output enables efficacious biological macromolecule transfers and cell fusions.

In the preferred embodiment, the high-voltage discharge generating means further comprises an input transformer means, an input driver means, a modulation means, a modulation control means, and an output transformer means. The input transformer means is adapted to transform the composite signal into a transformed composite signal. The input driver means is capable of driving the input transformer means. The modulation means is adapted to modulate the low-voltage system voltage into a modulated system voltage. The modulation control means, a capacitive-resistive network means, is adapted to control the operation of the modulation means. The output transformer means is capable of transforming the modulated system voltage into the high-voltage discharge output.

The preferred embodiment also includes a novel cell suspension receptacle. The receptacle comprises a hollow member and a grounding means. The ground means is a metallic electrode.

The high-voltage biological macromolecule transfer and cell fusion system is also capable of performing cell fusions. In general, electric field-induced cell fusions involve a two-step procedure. First, a high-frequency, nonuniform electric field is applied to a suspension of cells. The second step involves the application of a high-voltage, short duration, electric field pulse on the suspension.

One such cell fusion system is described, for example, in U. Zimmermann and J. Greyson, "Electric FieldInduced Cell Fusion", *BioTechniques*, September/October 1983. That system, using a Hewlett-Packard Model 214B pulse generator and a Toellner Model 7404P function generator, is capable of producing a high-frequency, nonuniform field in the range of 0–40 volts, at 10 KHz–5 MHz. The high-voltage discharge is generally a pulse having a duration from 0.1 microsecond to 99.9 microseconds, at 250 volts amplitude. The recharge time between each pulse is generally from 0.1 second to 9.9 seconds. The number of pulses generated is from 1 to 9. A commercial model of the Zimmermann system is manufactured by GCA Corp. of Chicago, Illinois.

Another system, manufactured by D.E.P. Systems, Inc. of Metamore, Michigan, is capable of providing a nonuniform field of 0–15 volts at 200–600 KHz. The discharging pulse of 250 volts has a duration from 0 to 300 microseconds. The cell suspension receptacle is capable of holding a suspension containing approximately 100,000 cells. The entire two-step procedure requires a completion time of about 10 minutes.

These prior art cell fusion systems are deficient in several aspects. First, the entire procedure is time consuming. Next, the time between each discharge of pulses may be long since the pulse discharging mechanism requires recharging. Moreover, the number of discharging pulses for each experiment may be limited. Further, although some of the parameters of the electric system may be varied, not all of them can be varied readily. Moreover, both of the electrodes need to be in contact with the cell suspension, enhancing the likelihood of contamination. Last, transferring the cell suspension, after the experiment, to a cultured flask is cumbersome. Generally, the cell fusion is initially carried out on a microscope slide, which is incapable of incubating the cell suspension.

One advantage of the present invention is that the novel biological macromolecule transfer and cell fusion system permits ready adjustment of operating parameters.

Another advantage of the present invention is that the novel biological macromolecule transfer and cell fusion system is capable of providing a continuous output of high voltage discharging pulses.

A further advantage of the present invention is that the novel biological macromolecule transfer and cell fusion system is capable of noncontact discharging, eliminating the likelihood of contaminating the suspension.

Another advantage of the present invention is that the novel biological macromolecule transfer and cell fusion system provides a simple operating procedure that permits the completion of the procedure in a short time.

A still further advantage of the present invention is that the novel biological macromolecule transfer and cell fusion system provides a novel cell suspension receptacle.

Another advantage of the present invention is that the novel biological macromelecule transfer and cell fusion system is capable of performing cell fusion.

Other objects, features, and advantages of the present invention will appear from the following detailed description of the best mode of a preferred embodiment, taken together with the accompanying drawings.

BRIEF DESCRIPTION OF THE DRAWINGS

FIG. 1 is an exemplary view of the novel high-voltage biological macromolecule transfer and cell fusion system of the present invention;

FIG. 2 is a block diagram of the electronics aspect of the system of FIG. 1;

FIG. 3A is a schematic of the high-voltage discharge charge generating means of FIG. 2;

FIG. 3B is a diagram of the output of the high-voltage discharge generating means of FIG. 3A;

FIG. 4A is a cross-section view of the novel suspension receptacle of FIG. 1; and FIG. 4B is a partial cross-section view of the suspension receptacle of FIG. 4A.

BEST MODE FOR CARRYING OUT THE INVENTION

Referring to FIG. 1, there is shown a high-voltage biological macromolecule transfer system, generally designated 12, for providing high-voltage discharge pulses to suspension 18. System 12 includes a probe or electrode 14 and a suspension receptacle 16 having a solution or suspension 18 of cells and biological macromolecules such as genes. As best shown in FIG. 2, system 12 comprises voltages source means 20, a frequency source means 22, a burst control means 24, a cycle control means 26, a pulse generating means 28, a pulse control means 30, a high-voltage discharge generating means 32, and master trigger switch 31.

More particularly, voltages source means 20 is adapted to transform a generally low input voltage into a direct-current base voltage, a generally low-voltage direct-current system voltage, and a system-enabling control signal. In the preferred embodiment, the low input voltage is generally either 120 volts or 220 volts alternating current. In addition, an amplitude switch, not shown, is used to select the amplitude A of the high-voltage output. Amplitude A may range from 0 volt to 10 KV. For the sake of convenience, the experimenter merely selects the numerical representation of the desired amplitude A when he positions a conventional variable voltage switch, not shown, at the desired amplitude. The actual amplitude of the low voltage input does not, of course, have an amplitude A. Using conventional techniques, the alternating-current input voltage, in the preferred embodiment, is transformed and rectified into a 12-volt direct-current base voltage and a 24-volt direct-current system voltage. In addition, the system-enabling control signal is fed into frequency source means 22.

Frequency source means 22 is capable of transforming the system-enabling control signal into pulse form. Also using conventional techniques, frequency source means 22 generates a chain of 20 Hz pulses.

Burst control means 24 is provided to control the burst time of the high-voltage discharge output. Burst control means 24, receiving a predetermined, arbitrary burst time signal B from a burst time switch, not shown, is capable of controlling the duration of such a burst. Burst and other parameters of the waveform of the high-voltage discharge pulses are shown in FIG. 3B. Burst control means 24, employing a conventional free-running, frequency-dividing counter, produces bursts B. The range of a burst B may be 0.05 second to 12.8 seconds, incremented in a binary fashion. This range is merely exemplary and is not limited to those values.

Similarly, cycle control means 26 is adapted to control the number of cycles CY in the high-voltage discharge output. Cycle control means 26, also employing a conventional counter, is capable of varying the number of cycles from zero to infinity, incremented by unity, e.g., 1, 2, 3, etc. The experimenter selects the number of cycles by selecting a numeral on a switch, not shown. Pulse generating means 28 is adapted to generate a pulse that will eventually evolve into the pulse of the high-voltage discharge output. Such a pulse, having a duration P, is generated by conventional clock means. In the preferred embodiment, duration of P is fixed at 62.5 microseconds. Again, this duration is merely exemplary and is not limited to that value.

Pulse control means 30 is provided to control the number of pulses NP within each burst B of the high-voltage discharge output. Pulse control means 30, also employing a conventional counter, may be selected to generate the number of pulses from one to 2,048, incrementable in a binary fashion, e.g., 2, 4, 8, 16, etc. These values are merely exemplary and are not limited to these values. The experimenter also selects the number of pulses on a switch, not shown.

The resultant signal that appears at the output of pulse control means 30 is a composite signal that has the characteristics of parameters B, CY, NP and P. These parameters were produced by burst control means 24, cycle control means 26, pulse control means 30 and pulse generating means 28, respectively.

High-voltage discharge generating means 32 is provided to transform the low-voltage system voltage and the composite signal into the high-voltage discharge output, whereby the high-voltage discharge output is capable of enabling efficacious biological macromolecule transfers or cell fusions. The waveform of the high-voltage discharge output is best shown in FIG. 3B.

In the preferred embodiment, as best shown in FIG. 3A, high voltage discharge generating means 32 comprises an input transformer means 34 for transforming the composite signal into a transformed composite signal. The composite signal is initially amplified by an input driver means 36, which is provided for driving input transformer means 34. The composite signal contains the characteristics of parameters such as pulse duration P, number of pulses NP, duration of burst B, and number of cycles CY. The transformed composite signal, at the output of input transformer means 34, is a pulse train representing the parameters B, CY, NP and P, with an amplitude of 24 volts maximum.

In addition, an input driver protection means 38 is provided. Input driver protection means 38 is used to prevent the back electromagnetic force from damaging input driver means 36 during the "turn off" period. As best shown in FIG. 3B, the "turn off" period is defined as that portion of the pulse duration P which falls from amplitude A to zero.

Discharge generating means 32 further comprises modulation means 42 for modulating the low-voltage, direct-current system voltage into a modulated system voltage. Modulation means 42, a conventional transistor in the preferred embodiment, employs the transformed composite signal as its base voltage. The output of transistor 42, at its collector, is a modulating composite signal. The modulating composite signal continues to contain the characteristics of parameters B, CY, NP and P. Transistor 42, therefore, uses the modulating composite signal to modulate direct-current system voltage into the modulated system voltage. The modulated sytem voltage, thus, contains the characteristics of parameters A, B, CY, NP and P.

A modulation control means 40 is provided to control the operation of modulation means 42. Means 40, a capacitive-resistive network means in the preferred embodiment, is capable of generating a negative voltage potential to "turn off" modulation means 42 as fast as possible during the "turn off" periods of the pulses of input transformer means 34.

Two modulation protection means are also provided -first means 46 and second means 44. Second means 44, a capacitive-inductive network means in the preferred embodiment that is generally referred to as a "snubber circuit", is adapted to reduce the power dissipation of modulating transistor 42 during the "turn off" period. First modulation protection means 46 is used to prevent the back electromagnetic force from damaging transistor 42.

Discharge generating means 32 also comprises an output transformer means 48 for transforming the modulated system voltage into the high-voltage discharge output. The high-voltage discharge output, containing the characteristics of parameters A, B, CY, NP and P, is a chain of continuously discharging pulses. This chain of pulses is illustrated in FIG. 3B.

In the preferred embodiment, biological macromolecule transfer and cell fusion system 12 includes a novel suspension receptacle 16. In addition, system 12 is operable without the necessity of immersing electrode 14 into suspension 18. Rather, electrode 14 is positioned above the top surface of suspension 18 in a noncontact fashion, e.g., one to 10 millimeters above the top surface.

Receptacle 16 is a hollow member 50 having at one end a metallic grounding member 52, as best shown in FIGS. 4A and 4B. In the preferred embodiment, hollow member 50 is a frusto-conical section having two ends 54, 56. Open end 54 has a diameter LD of approximately 1.000 cm, and closed end 56 a diameter SD of approximately 0.1800 cm. Grounding member 52, a steel spherical electrode, has a diameter BD of 0.200 cm. These numbers are also exemplary in nature. In addition, grounding member 52 is not limited to a spherical configuration. Moreover, receptacle 16 is of sufficient dimension as to contain a suspension having at least 10,000,000 cells.

In operation, a receptacle 16 containing a suspension 18 of cells and biological macromolecules is placed in system 12. Receptacle 16 and grounding electrode 52 were pre-sterilized. Electrode 14 is positioned above the top surface of suspension 18 in a non-contact fashion. The distance between electrode 14 and the top surface of suspension 18, a distance D, has an effect on the outcome of the experiment. For example, a small distance would enable the discharge of a greater amount of energy which in turn varies the membrane permeability of cells, permitting macromolecule transfers or cell fusions. Thus, the distance D, in addition to the other enumerated parameters, has an effect on the outcome of a biological macromolecule transfer or cell fusion experiment. The experimentor may vary this distance D to control the amount of discharging energy in order to optimize the efficiency of the biological macromolecule transfer or cell fusion.

Other desired parameters such as A, B, CY, NP and P are then selected by the experimenter. Master trigger switch 31 is then activated. High-voltage discharge generating means 32 produces a chain of continuously discharging high-voltage pulses into suspension 18. These high-voltage pulses contain the characteristics of the parameters A, B, CY, NP and P which were selected by the experimenter. All of these parameters, A, B, CY, D, NP and P, may be adjusted readily for the next experiment. In addition, system 12 completes the necessary biological macromolecule transfer or cell fusion in approximately one minute.

For the purpose of illustrating the present invention, the following examples are provided. The scope of the invention, however, is not intended to be limited thereto.

EXAMPLE 1

Gene Transfer

Murine thymidine kinase (mouse) defective cells, LM(TK−), were grown in an RPMI 1640 medium in an incubator. The 500 ml RPMI 1640 cultured medium is supplemented with 10% (final concentration) heat-inactivated fetal calf serum, 1 mM (milliMole) of MEM sodium pyruvate (Gibco cat. no. 320/1360), 5 mM of 200 mM L-glutamine, 5 ml of 100 × MEM non-essential amino acids (Gibco cat. no. 320/1140), 5 ml of a mixture of 10,000 units of penicillin and 10 μg of streptomycin (Gibco cat. no. 600/5140), and 10 mM of Hepes. The cells were trypsinized and washed with phosphate buffered saline (PBS) and resuspended in PBS for gene transfers. For a typical gene transfer, 100 μl of cell suspension containing $10^6$ cells were mixed with 5 μg of pTK5 DNA and the mixture was transferred to a receptacle 16 and subjected to the high voltage treatment of system 12. pTK 5 is a plasmid which has the 3400 base pair BamHI fragment of Herpes simplex I thymidine kinase gene inserted into the BamHI site of pBR322. The condition of the treatment was as follows:

Amplitude (A): 10 kV
Pulse Duration (P): 62.5 μ sec.
Number of Pulses (NP): 64
Burst time (B): 0.05 sec.
Number of cycles (CY): 20
Distance (D) between discharge electrode 14 and suspension 18: 0.4 cm After treatment, the mixture was diluted with 10 ml of RMPI 1640 medium and transferred to a 25 cm² Corning ® flask and incubated for two (2) days before a selective medium (RPMI 1640 supplemented with 15 μg/ml hypoxanthine, 0.2 μg/ml aminopterin, and 5 μg/ml thymidine) (HAT) was added. Medium changes were carried out every 3–4 days. After 9 days of incubation in the selective HAT medium, 21 cell clones appeared, indicating $TK^{30}$ transformant clones.

EXAMPLE 2

Cell Fusion

Spleen cells from Balb/c mouse immunized with bovine serum albumin were mixed with mouse myeloma SP 2/0 cells, centrifuged and resuspended in PBS in a ratio of 2:1 ($4 \times 10^7$ spleen cells and $2 \times 10^7$ SP 2/0 cells). The SP 2/0 Ag14 cells are referenced in Schulman and Kohler, *Nature Mag.*, No. 276, p. 269 (1978). After centrifugation, the cell mixture was resuspended in 0.1 ml of PBS. The cell suspension was then transferred into a receptacle 16 and subjected to the high voltage treatment of system 12. The condition of the treatment was as follows:

Amplitude (A): 7.5 kV
Pulse Duration (P): 62.5 μsec.
Number of Pulses (NP): 32
Burst time (B): 0.2 sec.
Number of cycles (CY): 10
Distance (D) between discharge electrode 14 and suspension 18: 0.5 cm After treatment, the mixture was slowly diluted with RPMI 1640 without fetal calf serum to 50 ml and centrifuged. The pellet was carefully resuspended in 20 ml of RPMI 1640 medium suppplemented with a selective HAT medium, as described previously. 0.2 ml of the cell suspension was plated into each well of a 24-well plate that contains $10^5$ macrophage cells which were seeded in the selective HAT medium at least 12 hours ago. Medium changes were carried out every 2–3 days whenever the situation required. After 10 days of incubation, cell clones appeared from 1 well out of 43 wells plated.

Since murine myeloma cells do not produce hypoxanthine-guanine-phosphoribosyl-transferase, and since murine spleen cells do not grow as culture cells, the appearance of clones survived in the culture medium supplemented with the selective HAT medium reflects the successful fusion between these two cell types.

It will be apparent to those skilled in the art that various modifications may be made within the spirit of the invention and the scope of the appended claims. For example, although receptacle 16 is shown as a frustroconical member 50 in the preferred embodiment, it may be of various shapes.

We claim:

1. A high-voltage biological macromolecule transfer and cell fusion system, said system being adapted to transform a low input voltage into a high-voltage discharge output, comprising voltages source means, said voltages source means being adapted to transform said generally low input voltage into a system-enabling control signal, a direct-current base voltage, and a generally low-voltage direct-current system voltage, said system voltage being capable of controlling the amplitude of said high-voltage discharge output;

a frequency source means for generating system-enabling control pulses, said frequency source means being adapted to transform said system-enabling control signal into said control pulses;

a burst control means for controlling the burst time of said high-voltage discharge output;

a cycle control means for controlling the number of cycles in said high-voltage discharge output;

a pulse generating means for generating the pulses that evolve into said high-voltage discharge output;

a pulse control means for controlling the number of pulses within each cycle of said high-voltage discharge output;

whereby said burst control means, said cycle control means, said pulse generating means and said pulse control means produce a composite signal; and a high-voltage discharge generating means for transforming said low-voltage system voltage and said composite signal into said high-voltage discharge output.

2. The high-voltage biological macromolecule transfer and cell fusion system as claimed in claim 1, wherein said high-voltage discharge generating means further comprises an input transformer means for transforming said composite signal into a transformed composite signal;

an input driver means for driving said input transformer means, said driver means being adapted to amplify said composite signal;

a modulation means for modulating said low-voltage, direct-current system voltage into a modulated system voltage;

a modulation control means for controlling the operation of said modulation means, said modulation control means includes a capacitive-resistive network means; and an output transformer means for transforming said modulated system voltage into said high-voltage discharge output.

3. The high-voltage biological macromolecule transfer and cell fusion system as claimed in claim 2, wherein said high-voltage discharge generating means further comprises an input driver protection means for protecting said input driver means;

a first modulation protection means for protecting said modulation means; and a second modulation protection means for protecting said modulation means, said second means includes a capacitive-inductive network means.

4. The high-voltage biological macromolecule transfer and cell fusion system as claimed in claim 1, 2, or 3, further comprising a hollow member, said hollow member adapted to receive a suspension of biological macromolecules and cells; and a grounding means, said grounding means being positioned adjacent said hollow member for facilitating the proper grounding of said system.

5. The high-voltage biological macromolecule transfer and cell fusion system as claimed in claim 4, further comprising a discharging electrode, said discharging electrode being positioned adjacent said suspension of biological macromolecules and cells in a non-contact fashion.

6. The high-voltage biological macromolecule transfer and cell fusion system as claimed in claim 4, wherein said hollow member is a frusto-conical section having an open end and a closed end.

7. The high-voltage biological macromolecule transfer and cell fusion system as claimed in claim 6, wherein said grounding member is a metallic electrode.

* * * * *